(12) United States Patent
Fojtik

(10) Patent No.: US 8,845,621 B2
(45) Date of Patent: Sep. 30, 2014

(54) APPARATUS FOR ROTATING MEDICAL DEVICES, SYSTEMS INCLUDING THE APPARATUS, AND ASSOCIATED METHODS

(75) Inventor: Shawn P. Fojtik, Park City, UT (US)

(73) Assignee: Distal Access, LLC, Park City, UT (US)

( * ) Notice: Subject to any disclaimer, the term of this patent is extended or adjusted under 35 U.S.C. 154(b) by 117 days.

(21) Appl. No.: 12/907,926

(22) Filed: Oct. 19, 2010

(65) Prior Publication Data

US 2012/0095447 A1   Apr. 19, 2012

(51) Int. Cl.
| | |
|---|---|
| A61B 17/00 | (2006.01) |
| A61B 17/32 | (2006.01) |
| A61B 17/16 | (2006.01) |
| A61B 17/17 | (2006.01) |
| A61M 25/01 | (2006.01) |
| A61B 10/04 | (2006.01) |
| A61B 17/22 | (2006.01) |
| A61M 25/09 | (2006.01) |
| A61B 17/3207 | (2006.01) |

(52) U.S. Cl.
CPC .......... *A61M 25/01* (2013.01); *A61B 2010/045* (2013.01); *A61B 2017/22078* (2013.01); *A61M 2025/09116* (2013.01); *A61B 17/320758* (2013.01); *A61M 25/09041* (2013.01); *A61B 2017/00469* (2013.01)
USPC ............... 606/1; 606/159; 606/170; 606/180; 606/113

(58) Field of Classification Search
None
See application file for complete search history.

(56) References Cited

U.S. PATENT DOCUMENTS

| | | | | |
|---|---|---|---|---|
| 24,005 | A | * | 5/1859 | Brooks ........................... 74/127 |
| 54,069 | A | * | 4/1866 | Hartford ......................... 74/127 |
| 377,783 | A | * | 2/1888 | Shaver ............................ 74/127 |
| 383,031 | A | * | 5/1888 | Allgoever ....................... 74/127 |

(Continued)

FOREIGN PATENT DOCUMENTS

| | | |
|---|---|---|
| DE | 38 04 849 A1 | 9/1988 |
| JP | 2003-290238 A | 10/2003 |

(Continued)

OTHER PUBLICATIONS

BCMA Medical Museum, Bone Drill Exhibit (1914-1930), BCMA Website http://bcmamedicalmuseum.org/object/993.1220.1 (Feb. 9, 2009 version).*

(Continued)

*Primary Examiner* — Lynsey Crandall
*Assistant Examiner* — Manolis Pahakis
(74) *Attorney, Agent, or Firm* — Durham Jones & Pinegar Intellectual Property Law Group

(57) ABSTRACT

A rooter includes a rotatable element, an actuator for causing the rotatable element to rotate, and a coupling feature for rotatably coupling an elongate medical instrument to the rotatable element. The rotatable element may be at least partially contained within the interior of a housing or another element that remains substantially stationary as the actuator causes the rotatable element to rotate. The rooter may be used with a variety of elongate medical instruments, such as needles, drill bits, trocars, wires, catheters, tubes, and other elongate instruments that are used to enable or effect medical procedures within the body of a subject. The rooter may be used for a variety of purposes, including, without limitation, the introduction of an elongate medical instrument into the body of a subject or its removal from the subject's body; removing, breaking up, or eliminating obstructions (e.g., blood clots, plaques, etc.) from the body of a subject; and obtaining samples from a subject's body.

7 Claims, 6 Drawing Sheets

(56) References Cited

U.S. PATENT DOCUMENTS

| | | | | |
|---|---|---|---|---|
| 385,414 | A * | 7/1888 | Huber | 74/127 |
| 505,165 | A * | 9/1893 | Hughes | 74/127 |
| 515,327 | A * | 2/1894 | Eggert | 74/127 |
| 532,145 | A * | 1/1895 | Defatsch | 74/127 |
| 537,681 | A * | 4/1895 | Furbish | 74/127 |
| 543,096 | A * | 7/1895 | Jones | 74/127 |
| 560,281 | A * | 5/1896 | Rauhoff | 74/424.89 |
| 568,460 | A * | 9/1896 | Schay | 74/127 |
| 575,734 | A * | 1/1897 | Rauhoff | 74/127 |
| 597,766 | A * | 1/1898 | Furbish | 74/127 |
| 621,401 | A * | 3/1899 | Davis | 74/127 |
| 624,122 | A * | 5/1899 | Stevenson | 74/127 |
| 652,137 | A * | 6/1900 | Olson | 74/127 |
| 654,150 | A * | 7/1900 | Hanna et al. | 74/127 |
| 666,508 | A * | 1/1901 | Furbish | 74/127 |
| 674,719 | A * | 5/1901 | Woodruff | 74/127 |
| 685,678 | A * | 10/1901 | Furbish | 74/127 |
| 700,970 | A * | 5/1902 | McFarland | 74/127 |
| 711,169 | A * | 10/1902 | LeBlanc | 74/127 |
| 722,332 | A * | 3/1903 | Stump | 74/127 |
| 756,388 | A * | 4/1904 | May | 74/127 |
| 791,766 | A * | 6/1905 | Furbish | 74/127 |
| 791,767 | A * | 6/1905 | Furbish | 74/127 |
| 799,968 | A * | 9/1905 | Blaske | 408/124 |
| 819,536 | A * | 5/1906 | Furbish | 74/127 |
| 873,296 | A * | 12/1907 | Chappelle | 74/127 |
| 924,372 | A * | 6/1909 | Peck | 74/127 |
| 924,878 | A * | 6/1909 | Baron | 74/127 |
| 938,341 | A * | 10/1909 | Ruple | 74/127 |
| 942,571 | A * | 12/1909 | Leland et al. | 74/127 |
| 942,572 | A * | 12/1909 | Leland | 74/127 |
| 973,881 | A * | 10/1910 | Rioux | 74/127 |
| 979,939 | A * | 12/1910 | Peglev | 74/127 |
| 1,023,023 | A * | 4/1912 | Wolin | 74/127 |
| 1,024,960 | A * | 4/1912 | Leopold | 74/127 |
| 1,033,615 | A * | 7/1912 | Peck | 74/127 |
| 1,054,142 | A * | 2/1913 | Plein | 74/127 |
| 1,061,773 | A * | 5/1913 | Nahlinger | 74/127 |
| 1,104,210 | A * | 7/1914 | Meredith | 451/117 |
| 1,104,863 | A * | 7/1914 | Baldwin | 451/117 |
| 1,134,511 | A * | 4/1915 | Carlson | 451/117 |
| 1,183,426 | A * | 5/1916 | Booth | 74/127 |
| 1,188,162 | A * | 6/1916 | Duggan | 74/127 |
| 1,206,589 | A * | 11/1916 | Pipshik | 451/117 |
| 1,268,309 | A * | 6/1918 | White | 451/117 |
| 1,290,489 | A * | 1/1919 | Bauer | 74/127 |
| 1,304,714 | A * | 5/1919 | Starrett | 74/127 |
| 1,330,053 | A * | 2/1920 | Booth | 74/127 |
| 1,415,251 | A * | 5/1922 | McLean | 74/127 |
| 1,415,822 | A * | 5/1922 | Fegley et al. | 74/127 |
| 1,422,411 | A * | 7/1922 | Borick | 74/127 |
| 1,460,201 | A * | 6/1923 | Leopold | 74/127 |
| 1,477,337 | A * | 12/1923 | Fegley et al. | 74/127 |
| 1,497,479 | A * | 6/1924 | Booth | 74/127 |
| 1,516,443 | A * | 11/1924 | Leopold | 74/127 |
| 1,531,086 | A * | 3/1925 | Fegley et al. | 74/127 |
| 1,578,866 | A * | 3/1926 | Swain | 74/127 |
| 1,704,067 | A * | 3/1929 | Wick | 74/127 |
| 1,821,194 | A * | 9/1931 | Wilcox | 74/127 |
| 1,838,957 | A * | 12/1931 | Orawiec | 74/127 |
| 1,904,679 | A * | 4/1933 | Fegley et al. | 74/127 |
| 1,971,289 | A * | 8/1934 | Abramson et al. | 74/127 |
| 1,971,290 | A * | 8/1934 | Abramson et al. | 74/127 |
| 3,049,018 | A * | 8/1962 | Lusskin et al. | 74/89.45 |
| 3,619,081 | A * | 11/1971 | Gruska et al. | 416/70 R |
| 3,869,936 | A * | 3/1975 | Taillardat | 74/424.87 |
| 3,955,578 | A | 5/1976 | Chamness et al. | |
| 4,273,128 | A | 6/1981 | Lary | |
| 4,306,599 | A * | 12/1981 | Kurahashi | 74/127 |
| 4,343,200 | A * | 8/1982 | Alworth et al. | 74/57 |
| 4,524,650 | A * | 6/1985 | Marks | 81/57.39 |
| 4,611,594 | A | 9/1986 | Grayhack et al. | |
| 4,685,344 | A * | 8/1987 | Horn et al. | 74/424.9 |
| 4,694,838 | A | 9/1987 | Wijayarthna et al. | |
| 4,926,858 | A | 5/1990 | Gifford, III et al. | |
| 5,024,565 | A * | 6/1991 | Pinand | 408/121 |
| 5,079,963 | A * | 1/1992 | Yamamoto et al. | 74/424.75 |
| 5,217,474 | A | 6/1993 | Zacca et al. | |
| 5,376,100 | A | 12/1994 | Lefebvre | |
| 5,527,326 | A | 6/1996 | Hermann et al. | |
| 5,787,953 | A * | 8/1998 | Jacobson | 160/168.1 R |
| 5,843,103 | A | 12/1998 | Wulfman | |
| 5,855,586 | A | 1/1999 | Habara et al. | |
| 5,911,722 | A * | 6/1999 | Adler et al. | 606/80 |
| 5,988,006 | A * | 11/1999 | Fleytman | 74/425 |
| 6,001,112 | A * | 12/1999 | Taylor | 606/159 |
| 6,015,381 | A | 1/2000 | Ouchi | |
| 6,090,118 | A | 7/2000 | McGuckin, Jr. | |
| 6,156,046 | A | 12/2000 | Passafaro et al. | |
| 6,258,101 | B1 | 7/2001 | Blake, III | |
| 6,270,508 | B1 * | 8/2001 | Klieman et al. | 606/147 |
| 6,602,262 | B2 | 8/2003 | Griego et al. | |
| 6,602,264 | B1 | 8/2003 | McGuckin, Jr. | |
| 6,685,722 | B1 | 2/2004 | Rosenbluth et al. | |
| 6,824,550 | B1 | 11/2004 | Noriega et al. | |
| 6,926,725 | B2 | 8/2005 | Cooke et al. | |
| 6,997,926 | B2 | 2/2006 | Gellman et al. | |
| 7,037,316 | B2 | 5/2006 | McGuckin, Jr. et al. | |
| 7,041,116 | B2 | 5/2006 | Goto et al. | |
| 7,101,378 | B2 | 9/2006 | Salameh et al. | |
| 7,179,269 | B2 | 2/2007 | Welch et al. | |
| 7,276,067 | B2 | 10/2007 | Bales et al. | |
| D556,527 | S * | 12/2007 | Russo et al. | D8/51 |
| 7,326,203 | B2 * | 2/2008 | Papineau et al. | 606/41 |
| 7,357,287 | B2 * | 4/2008 | Shelton et al. | 227/178.1 |
| 7,507,246 | B2 | 3/2009 | McGuckin et al. | |
| 7,559,934 | B2 | 7/2009 | Teague et al. | |
| 7,575,585 | B2 | 8/2009 | Goto et al. | |
| 7,621,923 | B2 | 11/2009 | Goldenberg | |
| 7,722,613 | B2 * | 5/2010 | Sutterlin et al. | 606/79 |
| 7,753,919 | B2 | 7/2010 | Kanamaru | |
| 7,819,887 | B2 | 10/2010 | McGuckin, Jr. et al. | |
| 7,822,458 | B2 * | 10/2010 | Webster et al. | 600/407 |
| 7,938,851 | B2 * | 5/2011 | Olson et al. | 623/1.11 |
| 7,946,198 | B2 * | 5/2011 | Gui et al. | 81/58.1 |
| 8,043,303 | B2 | 10/2011 | Razvi et al. | |
| 8,062,317 | B2 | 11/2011 | Mcguckin, Jr. et al. | |
| 8,125,097 | B1 * | 2/2012 | Lomerson et al. | 290/53 |
| 8,251,119 | B2 * | 8/2012 | Toti et al. | 160/168.1 R |
| 8,298,257 | B2 | 10/2012 | Sepetka et al. | |
| 8,414,543 | B2 | 4/2013 | McGuckin, Jr. et al. | |
| 2002/0069715 | A1 * | 6/2002 | Genco | 74/127 |
| 2002/0117534 | A1 * | 8/2002 | Green et al. | 227/176.1 |
| 2004/0064136 | A1 * | 4/2004 | Papineau et al. | 606/41 |
| 2005/0119615 | A1 | 6/2005 | Noriega et al. | |
| 2005/0143653 | A1 * | 6/2005 | Fukuda | 600/432 |
| 2005/0267323 | A1 | 12/2005 | Dorros et al. | |
| 2005/0273147 | A1 | 12/2005 | Israel | |
| 2006/0206128 | A1 * | 9/2006 | Conquergood et al. | 606/180 |
| 2006/0247607 | A1 | 11/2006 | Cornelius et al. | |
| 2007/0149893 | A1 * | 6/2007 | Heske et al. | 600/566 |
| 2007/0213634 | A1 | 9/2007 | Teague | |
| 2008/0033467 | A1 | 2/2008 | Miyamoto et al. | |
| 2008/0277445 | A1 | 11/2008 | Zergiebel et al. | |
| 2009/0270862 | A1 | 10/2009 | Arcenio | |
| 2009/0275970 | A1 * | 11/2009 | Leibowitz | 606/185 |
| 2011/0152920 | A1 | 6/2011 | Eckhouse et al. | |
| 2011/0282370 | A1 | 11/2011 | Levine et al. | |
| 2012/0238905 | A1 * | 9/2012 | Heske et al. | 600/566 |
| 2012/0239064 | A1 | 9/2012 | Cartier et al. | |
| 2012/0253186 | A1 | 10/2012 | Simpson et al. | |

FOREIGN PATENT DOCUMENTS

| | | | |
|---|---|---|---|
| JP | 2007-301392 A | 11/2007 | |
| JP | 2007-325925 A | 12/2007 | |
| JP | 2008-520351 A | 6/2008 | |
| JP | 2008-272488 A | 11/2008 | |
| JP | 2010-503479 A | 2/2010 | |
| RO | 117079 B1 * | 10/2001 | B25B 21/00 |

OTHER PUBLICATIONS

Wentzell T., Machine Design, Power Screws and Ball Screws, Thomson Delmar Learning, 2004 (obtained from http://www.uni.edu/~rao/MD-18%20Power%20screws.pdf on Dec. 6, 2013).*

(56) References Cited

OTHER PUBLICATIONS

Nagyszalanczy S., The Art of Fine Tools, The Taunton Press, 2000.*
BCMA Medical Museum, 993.1220.1: Bone Drill 1914-1930, Feb. 9, 2009 (obtaing from http://web.archive.org/web/20090209060158/http://bcmamedicalmuseum.org/object/993.1220.1).*
Eggert R., Chapter 13: Power Screws, Engineering Design, McGraw-Hill, 2004.*

U.S. Patent and Trademark Office "International Search Report" issued in corresponding PCT application PCT/US2011/056892, Jan. 30, 2012.
U.S. Patent and Trademark Office as the International Searching Authority, "International Search Report and Written Opinion," mailed Apr. 4, 2014, in corresponding PCT application PCT/US2013/069350.
The Crystal Reference Encyclopedia, Nitinol, 2005.

* cited by examiner

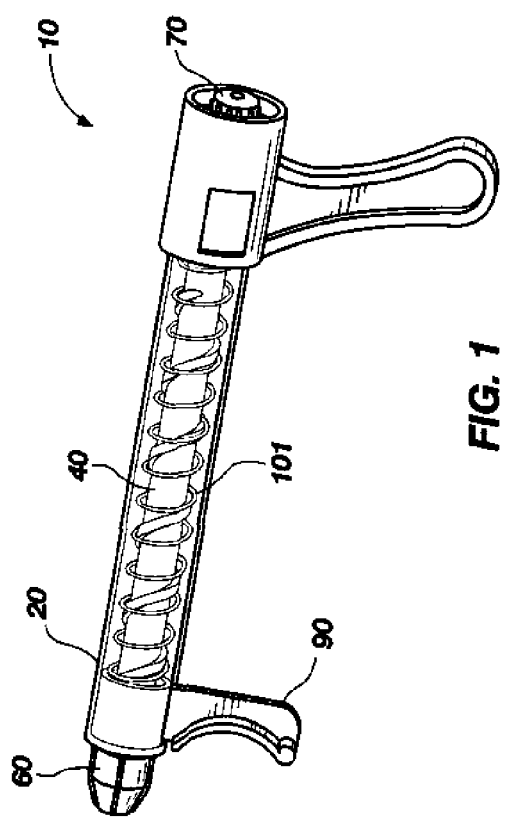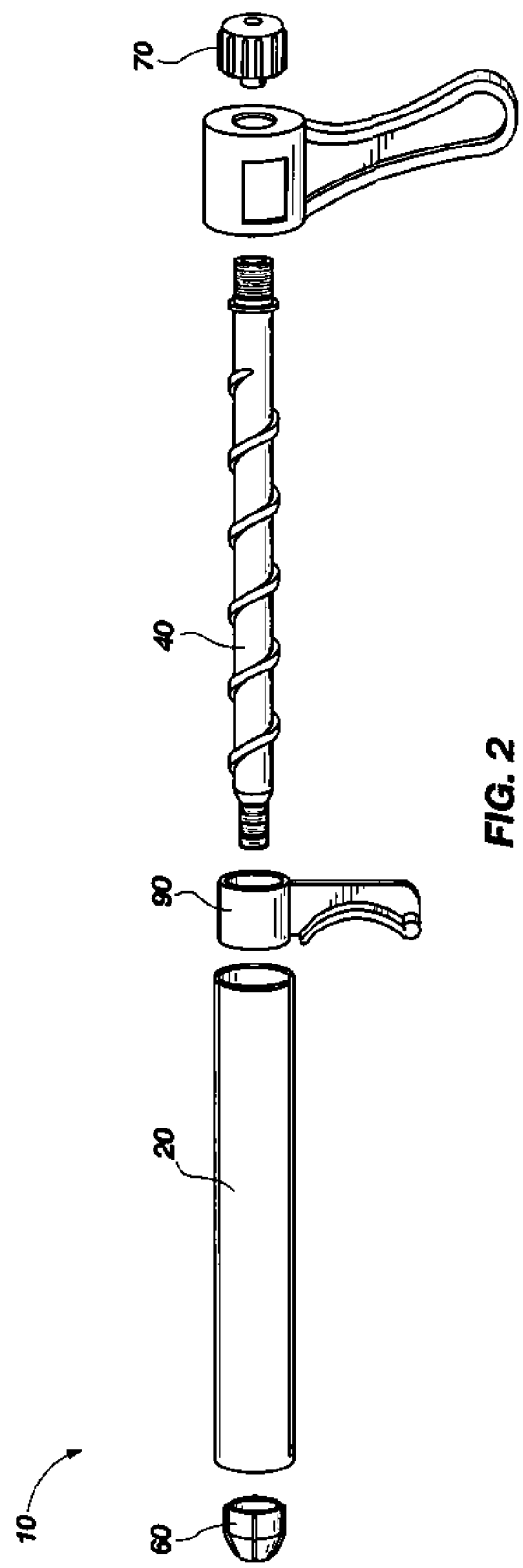

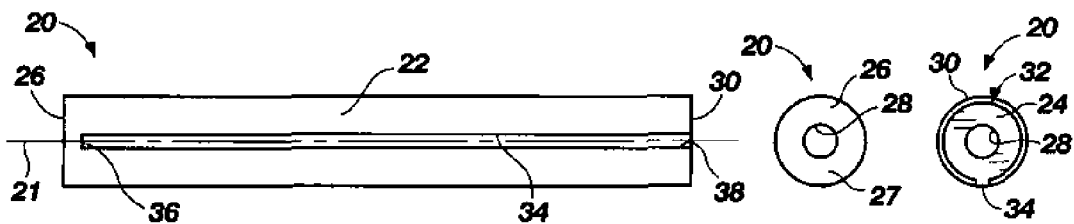
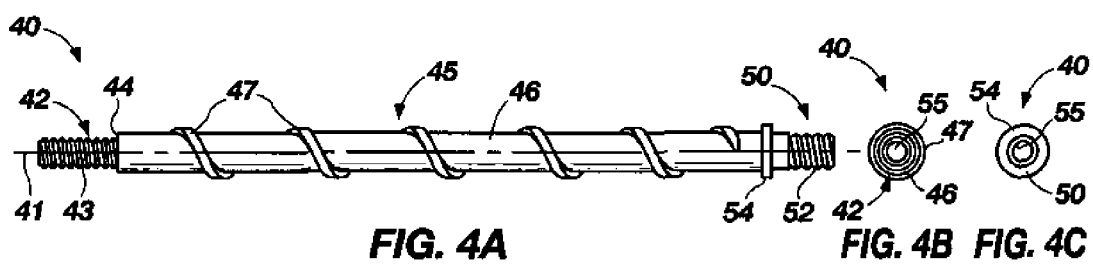
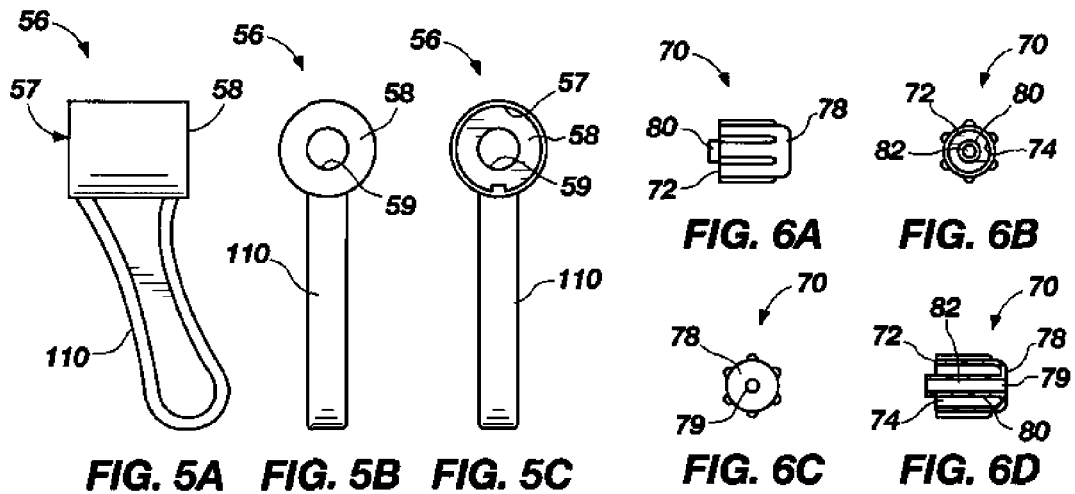
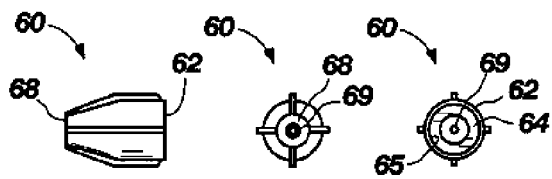
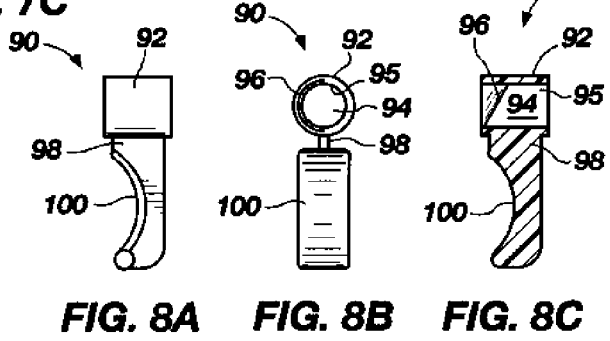

APPARATUS FOR ROTATING MEDICAL DEVICES, SYSTEMS INCLUDING THE APPARATUS, AND ASSOCIATED METHODS

TECHNICAL FIELD

The present invention relates generally to apparatuses and methods for rotating, or spinning, medical devices and, more specifically, to apparatuses and methods for manually spinning medical devices. In particular, the present invention includes apparatuses and methods for spinning needles, catheters, wires, trocars, and other elongate medical instruments that may be used to enable or effect a medical procedure within the body of a subject.

SUMMARY

In one aspect, the present invention includes various embodiments of an apparatus for causing an elongate medical instrument to rotate, or spin, about its longitudinal axis. Such an apparatus may be referred to herein as a "rooter." In a specific embodiment, such an apparatus includes a housing, a rotatable element within the housing, retention elements for securing the rotatable element in place relative to the housing, and an actuator that causes the rotatable element to rotate within the housing.

The rotatable element may be configured to engage an elongate medical instrument, such as a catheter, a needle, a wire, a trocar, or another elongate element that may be used to enable or effect a medical procedure within the body of a subject. In various embodiments, at least one end of the rotatable element, which is accessible from an end of the housing, may be configured to receive and retain the elongate medical instrument. In some embodiments, the rotatable element may comprise an elongate member with a longitudinal axis, about which the rotatable element may rotate, or spin. In a more specific embodiment, the rotatable element may include a helical ridge, similar to the thread of a bolt or screw.

The rotatable element may be disposed within an interior of the housing in a manner that enables the rotatable element to spin about its longitudinal axis. As the rotatable element rotates within the housing, which may remain substantially stationary (e.g., within a user's grasp, etc.), a medical element engaged by the rotatable element may rotate.

An actuator may be associated with the rotatable element in such a way as to cause the rotatable element to rotate. In a specific embodiment, the actuator may include an external element configured for manual operation, as well as an internal element that interacts with the rotatable element. In embodiments where the rotatable element has a helical ridge, the internal element of the actuator may be positioned between longitudinally adjacent locations of the helical ridge. In such embodiments, the actuator may move longitudinally relative to the rotatable element (e.g., in directions substantially parallel to the rotational axis of the rotatable element, etc.), while the internal element of the actuator and the helical ridge of the rotatable element interact with one another to cause the rotatable element, as well as any medical element engaged thereby, to rotate, or spin.

Longitudinal movement of the actuator may be enabled by an elongate slot that extends through the housing, along at least a portion of its length. The elongate slot may receive an intermediate element of the actuator, holding the actuator in place as it is moved along the length of the rotatable element.

The present invention also includes systems for effecting medical processes. A system of the present invention includes a rooter, as well as an elongate medical instrument, such as a catheter, a wire, a needle, a drill bit, a trocar, or another elongate element that may be used to enable or effect a medical procedure within the body of a subject, associated with the rooter. The rooter may be manually operable. As the rooter operates, it causes the elongate medical instrument to rotate or spin.

In another aspect, the present invention includes methods for rotating or spinning elongate medical instruments. In such a method, an elongate medical instrument is associated with (e.g., engaged by, etc.) a rotatable element of a rooter. Manual operation of an actuator of the rooter (e.g., as a user holds the rooter with one hand and moves the actuator with the user's thumb or finger, etc.) causes the rotatable element, along with the elongate medical instrument that has been secured to the rotatable element, to rotate or spin. The rotating elongate medical instrument may be used to effect a variety of medical procedures, depending at least in part upon the type of elongate medical instrument that has been assembled with the rooter.

Other aspects, as well as features and advantages of various aspects, of the present invention will become apparent to those of skill in the art from consideration of the ensuing description, the accompanying drawings, and the appended claims.

BRIEF DESCRIPTION OF THE DRAWINGS

In the drawings:

FIG. 1 is a perspective view of an embodiment of rooter of the present invention;

FIG. 2 is an exploded view of the embodiment of rooter shown by FIG. 1;

FIGS. 3A, 3B, and 3C are, respectively, bottom, distal end, and proximal end views of a housing of the embodiment of rooter depicted by FIGS. 1 and 2;

FIGS. 4A, 4B, and 4c are, respectively, side, distal end, and proximal end views of a rotatable element of the embodiment of rooter shown in FIGS. 1 and 2;

FIGS. 5A, 5B, and 5C are side, rear, and front views, respectively, of a cap of the embodiment of rooter illustrated by FIGS. 1 and 2;

FIGS. 6A, 6B, and 6C are, respectively, side, distal end, and proximal end views of a proximal retention element of the embodiment of rooter shown in FIGS. 1 and 2;

FIG. 6D is a cross-section taken through the length of the proximal retention element depicted by FIGS. 6A-6C;

FIGS. 7A, 7B, and 7C are, respectively, side, distal end, and proximal end views of a distal retention element of the embodiment of rooter illustrated by FIGS. 1 and 2;

FIGS. 8A and 8B are side and front views, respectively, of an actuator of the embodiment of rooter shown in FIGS. 1 and 2;

FIG. 8C is a cross-section through the length of the actuator shown in FIGS. 8A and 8B;

DETAILED DESCRIPTION

Figure 9A:
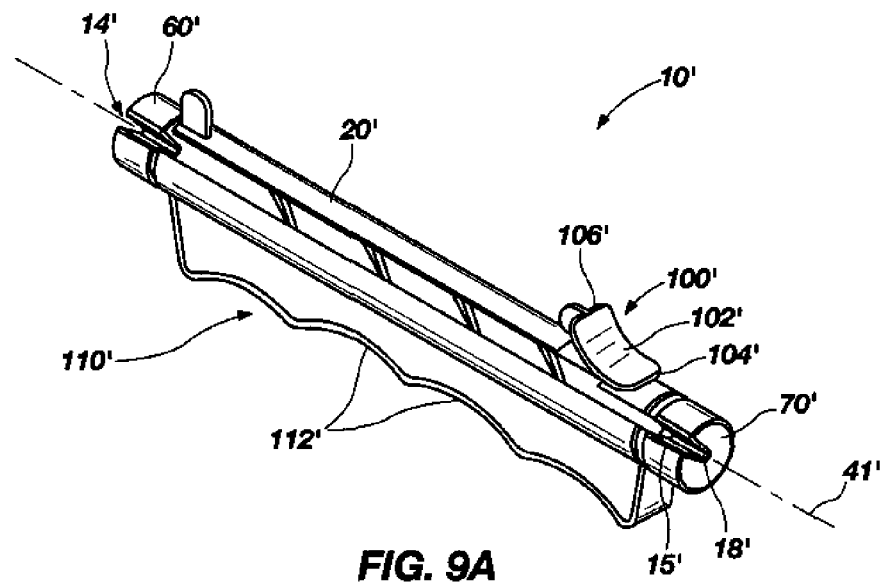
FIGS. 9A-9C are perspective, proximal end, and section views, respectively, of another embodiment of rooter of the present invention.

With reference to FIGS. 1 and 2, an embodiment of rooter 10 that incorporates teachings of the present invention is illustrated. Rooter 10 includes a housing 20, a rotatable element 40, a distal retention element 60 and a proximal retention element 70, and an actuator 90.

The housing 20, which is also shown in FIGS. 3A-3C, is an elongate element with an exterior 22 and a hollow interior 24. In the depicted embodiment, the housing 20 is cylindrical in shape, with a longitudinal axis 21 extending centrally through the length of the housing 20. The housing 20 includes a distal end 26 and an opposite, proximal end 30. A longitudinal slot 34 extends along a portion of the length of the housing 20.

The distal end 26, which is the end of the housing 20 that may be located farthest from an individual during use of the rooter 10 (FIGS. 1 and 2), is partially closed, as depicted by FIG. 3B. In a specific embodiment, the distal end 26 may include a circumferential lip 27 that defines an opening 28, which extends through the housing 20, from its exterior 22 to its interior 24. The opening 28 may be centered about the longitudinal axis 21 of the housing 20.

As seen in FIG. 3C, the proximal end 30 of the housing 20, which may be located closest to the individual during operation of the rooter 10, may include an opening 32 that exposes the interior 24 of the housing 20. In some embodiments, the proximal end 30 of the housing 20 may be configured to receive a cap 56 (FIGS. 5A-5C), which may at least partially close the opening 32 at the proximal end 30.

The longitudinal slot 34, illustrated in FIGS. 3A and 3C, extends through a wall of the housing 20, from the exterior 22 of the housing 20 to the interior 24 of the housing 20. In the embodiment depicted by FIG. 3A, the longitudinal slot 34 is substantially linear. A distal end 36 of the longitudinal slot 34 may be located adjacent to, but proximally spaced apart from, the distal end 26 of the housing 20. An opposite, proximal end 38 of the longitudinal slot 34 is located at or near (i.e., distally spaced apart from) the proximal end 30 of the housing 20.

The rotatable element 40 of the embodiment of rooter 10 (FIGS. 1 and 2) illustrated by FIGS. 4A-4C is an elongate element that is configured to be assembled with the housing 20 (FIGS. 3A-3C) of the rooter 10. In some embodiments, the rotatable element 40 may be tubular and, thus, include a conduit 55 extending through its length. A longitudinal axis 41 of the rotatable element 40 extends centrally or substantially centrally through a length of the rotatable element 40. In embodiments where the rotatable element 40 includes a conduit 55, the conduit 55 and the longitudinal axis 41 of the rotatable element 40 may be aligned (e.g., concentric, etc.).

In the depicted embodiment, the rotatable element 40 includes an intermediate portion 45, as well as a distal portion 42 and a proximal portion 50 at opposite ends of the intermediate portion 45.

The intermediate portion 45, which may be generally cylindrical in shape, includes a rotation facilitator 47. In the illustrated embodiment, the rotation facilitator 47 comprises a helical ridge, which protrudes from an outer surface 46 of the intermediate portion 45. In particular, the helical ridge 47 may wrap circumferentially around the intermediate portion 45. The helical ridge 47 extends along at least a portion of the length of the intermediate portion 45. In some embodiments, the helical ridge 47 may extend along only a part of the intermediate portion 45, as in the depicted embodiment, where the ends of the helical ridge 47 are spaced apart from corresponding ends of the intermediate portion 45.

The distal portion 42 of the rotatable element 40 may also be cylindrical in shape. In the embodiment shown in FIGS. 4A-4C, the distal portion 42 of the rotatable element 40 has a smaller diameter than the intermediate portion 45 of the rotatable element 40. Thus, a circumferential ledge 44 is present at the boundary between the distal portion 42 and the intermediate portion 45. The distal portion 42 may also be configured to pass through the opening 28 in the distal end 26 of the housing 20 (FIGS. 3A and 3C), and to protrude from the distal end 26. The distal portion 42 may be configured to engage or be engaged by the distal retention element 60 (FIGS. 7A-7C). In this regard, a distal portion 42 of some embodiments of a rotatable element 40 of a rooter 10 of the present invention may include one or more retention features 43, such as the helical thread shown in FIG. 4A.

The proximal portion 50 of the rotatable element 40 may likewise have a cylindrical shape. In some embodiments, the proximal portion 50 may be configured to protrude beyond the proximal end 30 of the housing 20 of a rooter 10 of the present invention. The proximal portion 50 may be configured to engage or be engaged by the proximal retention element 70 (FIGS. 6A-6D). Such engagement may, in some embodiments, be at least partially enabled by at least one retention feature 52, such as the helical thread illustrated by FIG. 4A.

A circumferential rim 54, which extends around and protrudes from the outer surface 46 of the rotatable element 40, may delimit, or define a boundary between, the intermediate portion 45 of the rotatable element 40 and its proximal portion 50. The circumferential rim 54 may provide a stop for an actuator 90 (FIGS. 8A-8C) that cooperates with the rotatable element 40 and is configured to cause the rotatable element 40 to rotate about its longitudinal axis 41.

In some embodiments, a rooter 10 (FIGS. 1 and 2) of the present invention may include a cap 56 configured to cooperate with the circumferential rim 54 to retain the rotatable element 40 within the interior of the housing 20. An embodiment of cap 56 that may be used as part of the rooter 10 (FIGS. 1 and 2) is shown in FIGS. 5A-5C. The cap 56 may be configured to be disposed over the opening 32 (FIGS. 3A and 3C) in the proximal end 30 of the housing 20. In a specific embodiment, the cap 56 may include a receptacle 57 that receives the proximal end 30 of the housing 20. An interior surface of an end 58 of the cap 56 may be configured to abut the circumferential rim 54 (FIGS. 4A and 4C) of the rotatable element 40 and an edge of the proximal end 30 of the housing 20, while an aperture 59 through the end 58 of the cap 56 may be configured to receive the proximal portion 50 of the rotatable element 40.

In some embodiments, a fixed handle 110 may protrude from the cap 56. A configuration of the fixed handle 110 may enable a user to at least partially grasp the rooter 10 (FIGS. 1 and 2) or hold it in place with a thumb or palm of a single hand.

The cap 56 may, in some embodiments, be held in place on the proximal end 30 of the housing 20 by way of the proximal retention element 70, an embodiment of which is depicted in FIGS. 6A-6D. The proximal retention element 70 is configured to be coupled with the proximal portion 50 (FIGS. 4A and 4C) of the rotatable element 40. More specifically, the proximal retention element 70 may have the appearance of a cap, with an open distal end 72 and a receptacle 74 that are configured to receive the proximal portion 50 of the rotatable element 40. In addition, at an opposite end of the receptacle 74 from the open distal end 72, the proximal retention element 70 may have a substantially closed proximal end 78.

The receptacle 74 may be configured to engage or to be engaged by the proximal portion 50 (FIGS. 4A and 4C) of the rotatable element 40. In a specific embodiment, the receptacle 74 may include at least one retention feature (not shown), such as a helical thread on an interior surface 75 of the receptacle 74, configured to mutually engage a corresponding retention feature 52 of the proximal portion 50 of the rotatable element 40.

An opening 79 may extend through the proximal end 78 of the proximal retention element 70. In some embodiments, such as that illustrated by FIGS. 6A-6D, the proximal retention element 70 and, in a particular embodiment, its opening 79 may be configured to receive and engage an elongate medical instrument, such as a wire (e.g., a guide wire, a wire used for other purposes, etc.), a catheter, or another elongate element that may be used to enable or effect a medical procedure within the body of a subject. In the illustrated embodiment, the opening 79 through the proximal end 78 of the proximal retention element 70 communicates with a conduit 82 of a male member 80. The male member 80 extends through the receptacle 74 of the proximal retention element 70. When used with an embodiment of rotatable element 40 (FIGS. 4A-4C) that includes a conduit 55, the male member 80 of the proximal retention element 70 may be configured for insertion into the conduit 55.

In some embodiments, the proximal retention element 70 may be configured to engage an elongate medical instrument 200 (FIG. 13) in a manner that causes the elongate medical instrument 200 to rotate as the proximal retention element 70 rotates. For example, and not to limit the scope of the present invention, the surfaces that define the opening 79 through the proximal end 78 of the proximal retention element 70 may be configured to lock onto, grasp, or engage a surface 208 of the elongate medical instrument 200. As another non-limiting example, the proximal retention element 70 may include one or more features (e.g., a retention slot, a locking feature, etc.) that communicate or are otherwise associated with the opening 79 through the proximal end 78 to enable selective locking, grasping, or other engagement of the surface 208 of the elongate medical instrument 200. In yet another non-limiting example, the proximal retention element 70 may be configured to couple with a separate device (not shown) that locks onto, grasps, or otherwise engages the surface 208 of the elongate medical instrument 200.

The distal retention element 60, an embodiment of which is illustrated by FIGS. 7A-7C, may also have the general appearance of a cap, with an open proximal end 62, an interior receptacle 64 that communicates with proximal end 62, and a substantially closed distal end 68. The proximal end 62 and the receptacle 64 are configured to receive the distal portion 42 (FIGS. 4A and 4B) of the rotatable element 40. In some embodiments, the receptacle 64 includes one or more retention features (not shown), which may be configured to mutually engage a corresponding retention feature 43 of the distal portion 42 of the rotatable element 40, such as a helical thread carried by the surface 65 of the depicted receptacle 64.

The distal end 68 of the distal retention element 60 may include an opening 69, which may be configured to receive an elongate medical instrument 200 (FIG. 13), such as a catheter, wire (e.g., a guide wire, a wire used for other purposes, etc.), a needle, a trocar, or another elongate element that may be used to enable or effect a medical procedure within the body of a subject. When such a distal retention element 60 is configured for assembly with an embodiment of rotatable element 40 (FIGS. 4A-4C) that includes a conduit 55 extending therethrough, the opening 69 through the distal end 68 of the distal retention element 60 may be configured for alignment and/or communication with the conduit 55.

In addition to being configured to receive an elongate medical instrument 200 (FIG. 13), some embodiments of distal retention elements 60 may be configured to lock onto, grasp, or otherwise engage, or at least partially engage, the elongate medical instrument 200. Without limiting the scope of the present invention, a distal retention element 60 may include a locking element (not shown) at its distal end 68, external or internal (i.e., within the opening 69 in the distal end 68) threading, internal features (e.g., ribs, etc.) that lock onto, grasp, or otherwise engage an outer surface 208 of the elongate medical instrument 20Q, other locking features, or the distal retention element 60 may be configured to couple with a separate device (not shown) that locks onto, grasps, or otherwise engages the surface 208 of the elongate medical instrument 200.

Turning now to FIGS. 8A-8C, an embodiment of an actuator 90 that may be used with the embodiments of housing 20 and rotatable element 40 shown in FIGS. 4A-4C is illustrated. In particular, the actuator 90 may be configured to interact with the rotatable element 40 in a manner that causes the rotatable element 40, when assembled with the housing 20, to rotate about its longitudinal axis 41. In various embodiments, the actuator 90 includes one or more drive features 96 for causing the rotatable element 40 to rotate.

In the depicted embodiment, the actuator 90 comprises a cylindrical element 92 with an aperture 94 extending through its length. The aperture 94 is configured to receive the rotatable element 40 (FIGS. 4A-4C) and, more specifically, to receive the intermediate portion 45 of the rotatable element 40, enabling the cylindrical element 92 of the actuator 90 to move along the length of the rotatable element 40. The interior surface 95 of the cylindrical element 92—i.e., the surface of the aperture 94—may define one or more drive features 96. In the specific embodiment shown in FIGS. 8B and 8C, the drive features 96 may be configured to engage a corresponding rotation facilitator 47 of the intermediate portion 45 of the rotatable element 40. More specifically, the drive features 96 may engage the rotation facilitator 47, which may comprise a helical ridge, of the intermediate portion 45 of the rotatable element 40.

In addition to including an element configured to cause the rotatable element 40 to rotate, an actuator 90 of a rooter 10 of the present invention may include an intermediate element 98, which may be configured to reside within and move back and forth through the longitudinal slot 34 in the housing 20.

On an opposite side of the intermediate element 98, the actuator 90 may include a manual trigger 100, which may be engaged by a portion of a user's hand, such as a finger or thumb.

In some embodiments, such as that depicted by FIG. 1, a rooter 10 that incorporates teachings may also include a return element 101, such as a spring, that causes the actuator 90 and its manual trigger 100 to return to or substantially to an initial position. When the manual trigger 100 is moved in a first direction (e.g., proximally, etc.), energy may be stored in the return element 101. When the manual trigger 100 is released, the resilience of the return element 101, and the energy stored within the return element 101, may cause the actuator 90, including the manual trigger 100, to move in an opposite, second direction (e.g., distally, etc.) along the lengths of the housing 20 and the rotatable element 40 of the rooter 10. As illustrated by FIG. 1, the return element 101 may comprise an internal compression spring, which, in the depicted embodiment, is compressed between an edge of the cylindrical element 92 of the actuator 90 and an interior surface of the end 58 of the cap 56 as the manual trigger 100 and, thus, the cylindrical element 92 are drawn proximally along the rotatable element 40 and the housing 20. Of course, other embodiments of return elements 101, including other types of internal springs, external springs, and other apparatus that will cause the actuator 90 to automatically reverse its position.

In some embodiments, the automatic return of the actuator 90 to its initial position may also cause the rotatable element 40 to rotate in its opposite direction.

In other embodiments, including embodiments where movement of the rotatable element 40 in a single direction (e.g., clockwise or counterclockwise) is desired or oscillatory movement of the rotatable element 40 is not desired, the actuator 90 of a rooter 10 of the present invention may be configured to return to its initial position without causing further rotation of the rotatable element 40. Without limiting the scope of the present invention, an actuator 90 may disengage the rotation facilitator 47 of the rotatable element 40 as the actuator 90 returns to its initial position, or the actuator 90 may otherwise be configured to return to its initial position without disengaging the rotation facilitator (e.g., the actuator 90 may include a ratchet mechanism that allows it to return to its initial position without disengaging the rotation facilitator 47, etc.).

Returning reference to FIG. 2, assembly of a rooter 10 that includes the above-described elements may be accomplished by assembling the rotatable element 40 and the actuator 90. The distal portion 42 of the rotatable element 40 may be introduced into and through the aperture 94 of the cylindrical element 92 of the actuator 90. As the rotatable element 40 is pushed distally through the aperture 94, the drive features 96 of the actuator may engage the rotation facilitator 47 that protrudes from the outer surface 46 of the intermediate portion 45 of the rotatable element 40.

Assembly of the housing 20 and the actuator 90 may include introduction of the cylindrical element 92 of the actuator into the opening 32 at the proximal end 30 of the housing 20, with the intermediate element 98 of the actuator 90 located within the longitudinal slot 34 through the housing 20. The manual trigger 100 is, of course, located outside of the housing 20, and protrudes from the housing 20.

The distal portion 42 of the rotatable element 40 may be introduced into the opening 32 at the proximal end 30 of the housing 20 to assemble the rotatable element 40 with the housing 20. The distal portion 42 of the rotatable element 40 is then moved distally through the interior 24 of the housing 20, until the distal portion 42 reaches the distal end 26 of the housing 20. The distal portion 42 of the rotatable element 40 may then be introduced into and through the opening 28 in the distal end 26 of the housing 20, until the distal portion 42 of the rotatable element 40 protrudes from the distal end 26 of the housing 20.

With the distal portion 42 of the rotatable element 40 protruding from the distal end 26 of the housing 20, the longitudinal position of the rotatable element 40 within the interior 24 of the housing 20 may be fixed or substantially fixed by coupling the distal retention element 60 to the distal portion 42 of the rotatable element 40.

When the housing 20 and the rotatable element 40 are assembled, the proximal portion 50 of the rotatable element 40 protrudes beyond the proximal end 30 of the housing 20. To hold the rotatable element 40 and the actuator 90 within the interior 24 of the housing 20, the cap 56 may then be placed over the proximal end 30 of the housing 20. More specifically, the receptacle 57 of the cap 56 may be positioned over the proximal end 30 of the housing 20. Additionally, the proximal portion 50 of the rotatable element 40 may be aligned with the aperture 59 through the end 58 of the cap 56.

As the cap 56 moves distally relative to the housing 20 and the rotatable element 40, the proximal portion 50 of the rotatable element 40 may be positioned around proximal portion 50 of the rotatable element 40.

The cap 56 may be held in place relative to the proximal end 30 of the housing 20 by coupling the proximal retention element 70 to the protruding proximal portion 50 of the rotatable element 50.

Other embodiments of rooters that incorporate teachings of the present invention are shown in FIGS. 9A-11. Features of those embodiments may, unless otherwise described, operate in the same manner or in a manner similar to the corresponding elements of the rooter 10 that has been described in reference to FIGS. 1-8C.

Figure 9B:
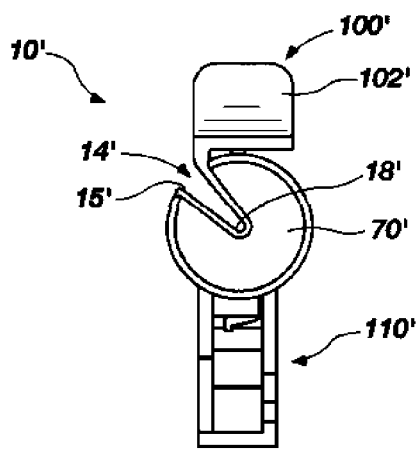
Figure 9C:
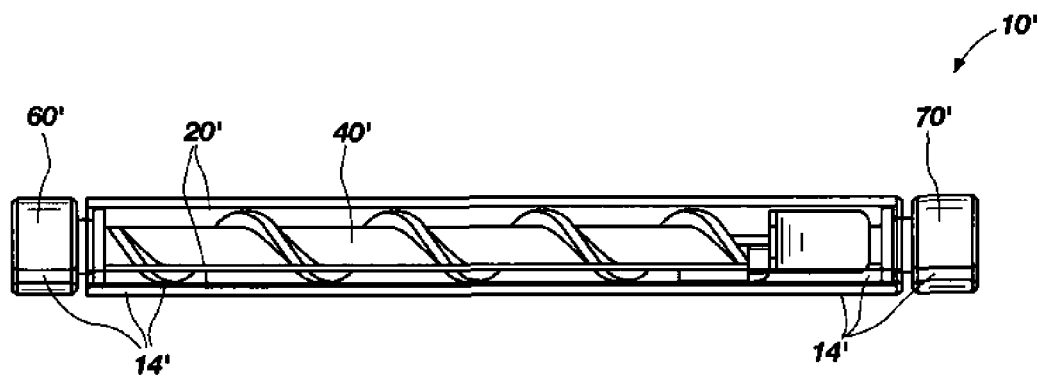

In FIGS. 9A-9C, an embodiment of rooter, 10' is depicted that includes a longitudinal slot 14' that extends the entire length of the device. The longitudinal slot 14' includes portions that extend through the distal retention element 60', the housing 20' and rotatable element 40', and the proximal retention element 70'. In the depicted embodiment, the longitudinal slot 14' is wider at its opening 15' (i.e., at the surfaces or circumferences of one or more of the distal retention element 60', the housing 20' (and, optionally, the rotatable element 40'), and the proximal retention element 70') than at its closed edge 18', which, in some embodiments, may be located at or extend to a location just beyond a longitudinal axis 41' of the rotatable element 40' of the rooter 10'. Slots 14' that are tapered in this manner may be configured to receive and retain (e.g., by interference fit, etc.) elongate medical instruments 200 (FIG. 13) of a variety of different diameters or gauges.

FIGS. 9A-9C also illustrate another embodiment of manual trigger 100' and handle 110' that may be used with a rooter (e.g., rooter 10', etc.) according to the present invention. The manual trigger 100' includes a concave surface 102' with a proximal portion 104' oriented generally parallel with the housing 20' of the rooter 10' and a distal portion 106' extending away from the housing 20'. The configuration and orientation of the manual trigger 100' enable it to be easily moved along the length of the housing 20', particularly when a user wraps his or her fingers around the housing 20'. In order to accommodate the user's fingers, and to enhance the user's grasp on the housing 20', a handle 110' may be positioned on an opposite or substantially opposite (e.g., diametric, etc.) side of the housing 20' from the manual trigger 100'. In the depicted embodiment, the handle 110' is an elongate element with a plurality of concave indentations 112' for receiving the user's fingers.

Figure 10:
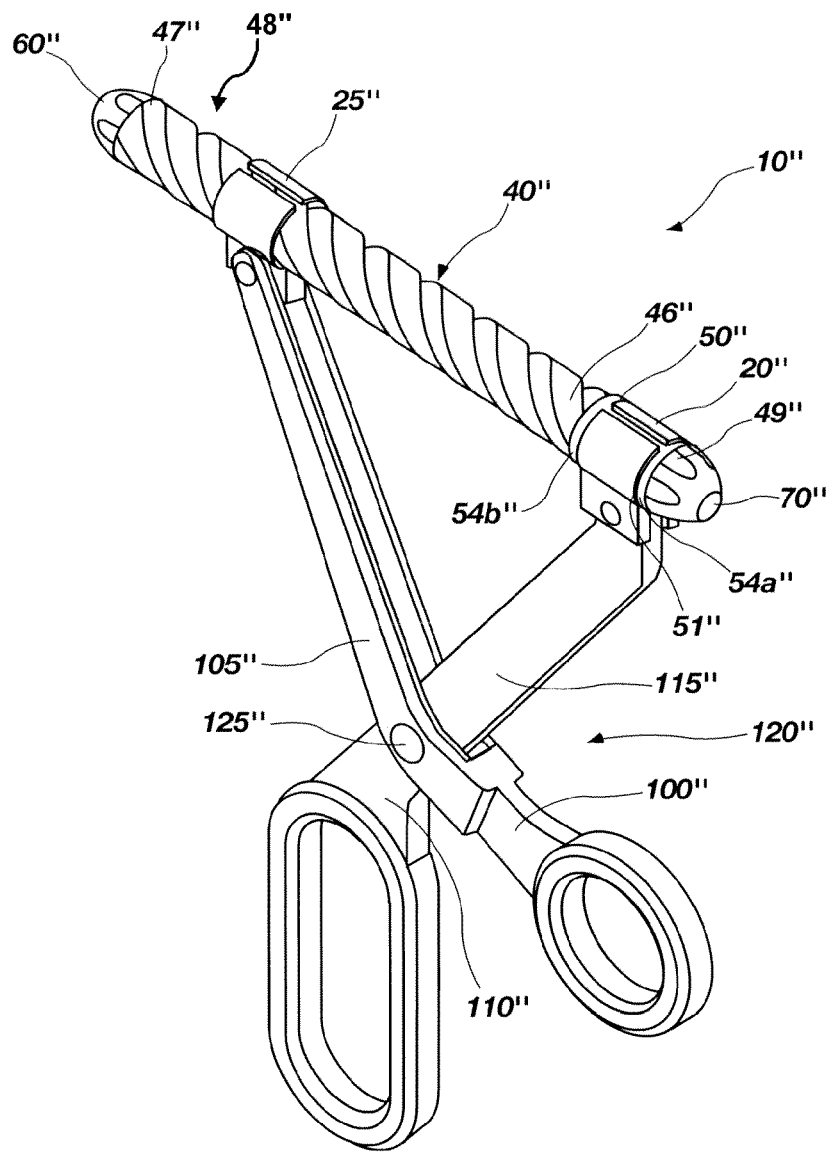
FIG. 10 illustrates an embodiment of rooter with a pair of connected handles.

Referring now to FIG. 10, an embodiment of rooter 10" that lacks a housing, and includes a scissor-like handle 120" is shown. Instead of a housing, rooter 10" includes a stationary sleeve 20" and a translatable sleeve 25". The stationary sleeve 20" and the translatable sleeve 25" both include cylindrical openings.

Stationary sleeve 20" is configured to be longitudinally retained within a retention section 51" of a rotatable element 40" of the rooter 10". The retention section 51" is defined by a pair of spaced apart circumferential rims 54a" and 54b" protruding from the outer surface 46" of the rotatable element 40", and a smooth, cylindrically shaped portion of the outer surface 46" located between the circumferential rims 54a" and 54b". Although the retention section 51" is depicted in FIG. 10 as being located near the proximal portion 50" of the rotatable element 40", rotatable elements with retention portions at other longitudinal locations are also within the scope of the present invention.

The translatable sleeve 25" is configured to interact with a rotation facilitator 47" of the rotatable element 40". In the depicted embodiment, the translatable sleeve 25" may be configured like, or similar to, the cylindrical element 92 of the actuator 90 described in reference to FIGS. 8A-8C.

Figure 13:
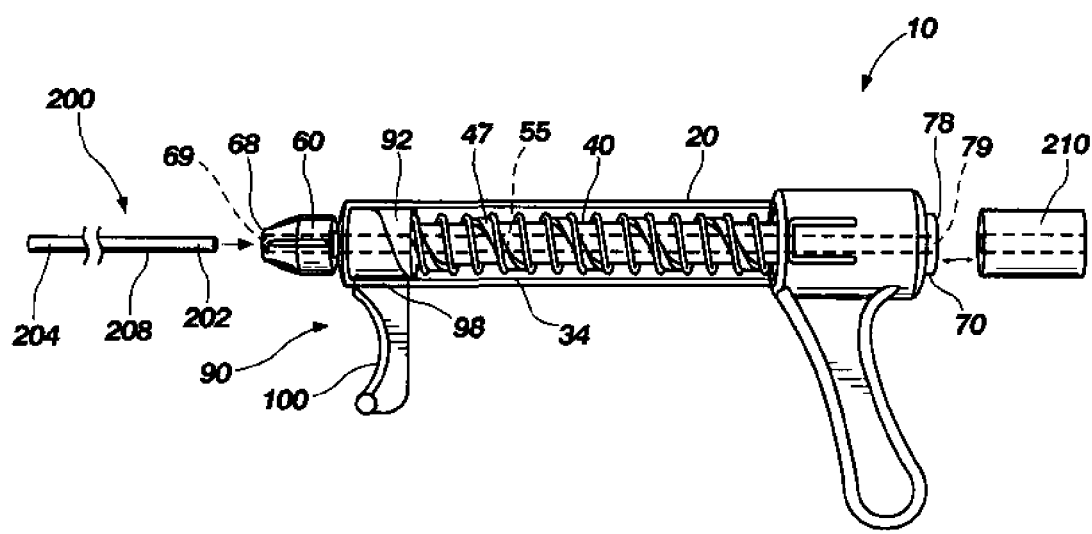
FIG. 13 shows a manner in which an elongate medical instrument may be assembled with a rooter of the present invention.

Retention elements 60" and 70" on opposite ends 48" and 49", respectively, of the rotatable element 40". In the depicted embodiment, retention element 60" may prevent movement of the translatable sleeve 25" beyond its corresponding end 48" of the rotatable element 40". (Of course, in embodiments where the retention section 51" of the rotatable element 40" is located at or nearer to a distal portion 42" of the rotatable element 40", the proximal retention element 70" located adjacent to a proximal portion 50" of the rotatable element 40" may prevent the translatable sleeve 25" from moving beyond its corresponding end 49" of the rotatable element 40"). One or both retention elements 60" and 70" may be configured to engage an elongate medical instrument 200 (FIG. 13).

The handle 120" includes two handle members 100" and 110". The handle members 110" and 100" extend from the stationary sleeve 20" and the translatable sleeve 25", respectively. In the depicted embodiment, each handle member 100", 110" is pivotally associated with its corresponding sleeve 20", 25". Handle members 100" and 110" cross at somewhat intermediate locations 105" and 115", respectively, and are joined to one another at those locations by a hinge 125". As the handle members 100" and 110" are drawn together or forced apart, the translatable sleeve 25" interacts with the rotation facilitator 47" of the rotatable element 40", causing the rotatable element 40" to rotate.

Figure 11:
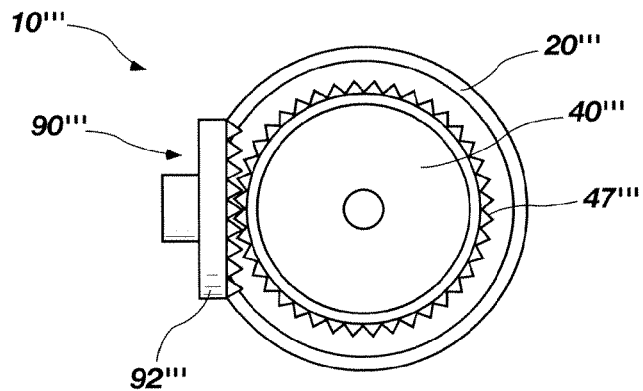
FIG. 11 depicts an embodiment of gear-driven rooter.

In another embodiment, shown in FIG. 11, a rooter 10''' of the present invention may include an actuator 90''' that comprises a rotatable gear 92'''. As the rotatable gear 92''' of the actuator 90''' rotates (e.g., by use of a thumb to rotate the actuator 90''' or a feature thereof, etc.), it engages another gear of a rotation facilitator 47''' associated with (e.g., surrounding, at least partially surrounding, etc.) the rotatable element 40''' of rooter 10''' ((e.g., extending circumferentially around a portion of the rotatable element 40''', etc.). In such an embodiment, the actuator 90''' may remain in a stationary position along the length of the rooter 10''' (i.e., along the lengths of the housing 20''' and the rotatable element 40''') as the rotatable element 40''' rotates.

Figure 12A:
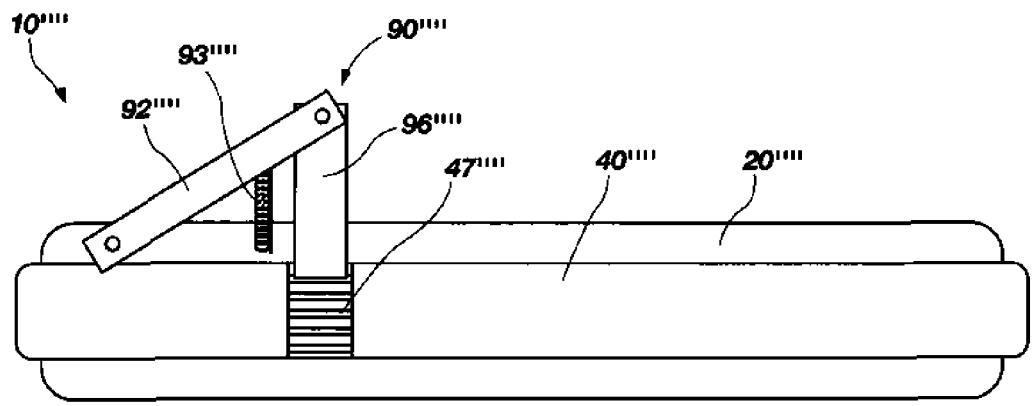
FIGS. 12A-12C shown an embodiment of rooter that rotates under control of a rack and pinion mechanism.
Figure 12B:
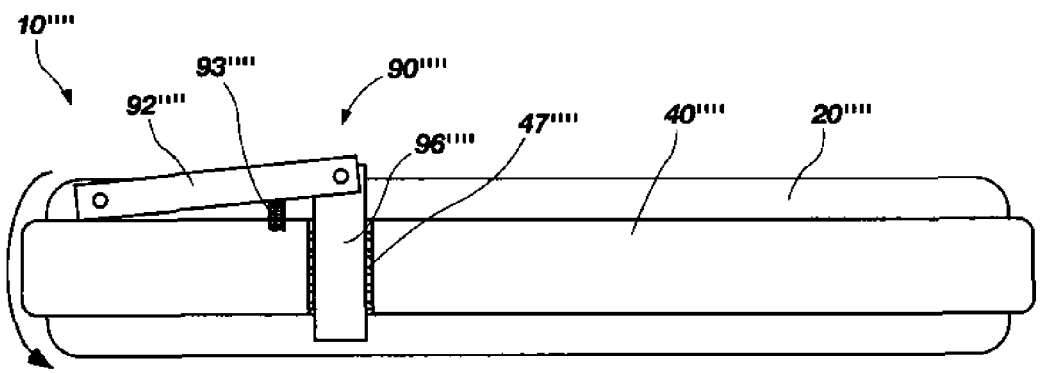
Figure 12C:
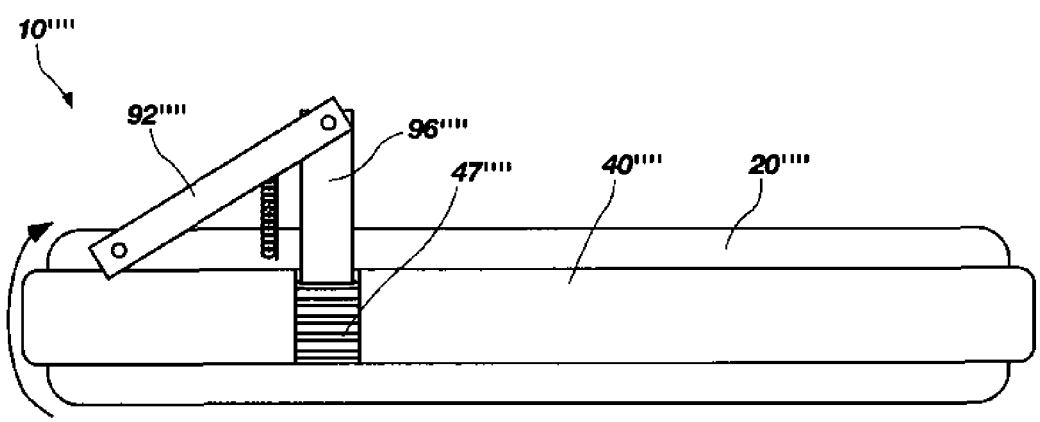

FIGS. 12A-12C depict an embodiment of rooter 10'''' in which the actuator 90'''' includes a manual trigger 92'''' and a gear rack 96''''. The manual trigger 92'''' is translatably associated with the housing 20'''' of the rooter 10'''' (e.g., pivotally, such as in the depicted embodiment; like a push button, etc.). In various embodiments, the manual trigger 92'''' may be operated with a user's thumb or finger. In some embodiments, a resilient element 93'''' (e.g., a spring, etc.) may be associated with the manual trigger 92'''' in such a way as to cause the manual trigger 92'''' to return to its initial position after the manual trigger 92'''' has been depressed or otherwise actuated.

The gear rack 96'''' of the actuator 90'''' may be associated with the manual trigger 92'''' in such a way that, when the manual trigger 92'''' is depressed or otherwise actuated, the gear rack 96'''' moves in a desired direction. In the depicted embodiment, depression of the manual trigger 92'''' causes the gear rack 96'''' to move in a first direction across, or transverse to, the length of a rotatable element 40'''' of the rooter 10'''', which is disposed within an interior of the housing 20''''. When the manual trigger 92'''' is released, the resilient element 93'''', if any, may cause the gear rack 96'''' to move in an opposite, second direction across the rotatable element 40''''.

A gear 47'''' with teeth that are configured and spaced to mesh with teeth of the gear rack 96'''' is positioned along the length of the rotatable element 40'''' at a location where the gear 47'''' will cooperate with the gear rack 96''''. As the manual trigger 92'''' moves and causes the gear rack 96'''' to move, the gear rack 96'''' rotates the gear 47''''. Rotation of the gear 47'''', in turn, rotates the rotatable element 40'''', along with any elongate medical instrument 200 (FIG. 13) that has been directly or indirectly coupled to the rotatable element 40''''.

Turning now to FIG. 13, a rooter that incorporates teachings of the present invention (rooter 10 is shown, merely to provide an example) may be used to rotate an elongate medical instrument 200. Non-limiting examples of elongate medical instruments 200 that may be used with a rooter of the present invention include catheters, wires (e.g., guide wires, etc.), needles, drill bits, trocars, and other elongate elements that may be used to enable or effect medical procedures within the body of a subject. Depending upon their intended or desired use, these elongate medical instruments may be configured with a variety of tips or distal elements, or with accessories such as balloons, brushes, stents, electrodes, sensors, cutting elements, optics, or wiring.

In use, a proximal end 202 of an elongate medical instrument 200 may introduced into an opening 69 in the distal end 68 of the distal retention element 60 of the rooter 10. When the elongate medical instrument 200 comprises a relatively short device, such as a needle, trocar, or the like, insertion of the proximal end 202 of the elongate medical instrument 200 into the opening 69 may at least partially couple the elongate medical instrument 200 to the rooter 10 without inserting the elongate medical instrument 200 further into the rooter 10. In embodiments where the elongate medical instrument 200 comprises a longer device, such as a catheter, wire or the like, its proximal end 202 may be inserted only into the opening 69 of the distal end 68 of the distal retention element 60, or the proximal end 202 may be inserted further into the rooter 10. Without limiting the scope of the present invention, the proximal end 202 of the elongate medical instrument 200 may also be pushed proximally through the conduit 55 of the rotatable element 40 of the rooter 10, and through the opening 79 through the proximal end 78 of the proximal retention element 70 of the rooter 10.

With the elongate medical instrument 200 in place, it may be rotationally coupled to the rooter 10. In embodiments where the distal retention element 60 and/or the proximal retention element 70 of the rooter 10 includes features that lock onto, grasp, or otherwise engage a surface 208 of the elongate medical instrument 200, rotational coupling of the elongate medical instrument 200 to the rooter 10 occurs during assembly of the elongate medical instrument 200 with the rooter 10. In other embodiments, at least one separate locking device 210 may be assembled with and lock onto, grasp, or otherwise engage the surface 208 of the elongate medical instrument 200, then each locking device 210 may be coupled to the distal retention element 60 or the proximal retention element 70 of the rooter 10. Rotational coupling of the elongate medical instrument 200 to the distal retention element 60 or the proximal retention element 70 may be effected in a manner that causes the elongate medical instrument 200 to rotate as the distal retention element 60 and/or the proximal retention element 70 rotates.

A distal end 204 of the elongate medical instrument 200 may be introduced into a body of a subject at a desired location. In some embodiments, the distal end 204 may be inserted into the subject's body before the elongate medical instrument 200 is assembled with the rooter 10. In other embodiments, the rooter 10 may be assembled with an elongate medical instrument 200 that has already been introduced, or at least partially introduced, into the subject's body.

Rotation of the elongate medical instrument 200 (e.g., about its longitudinal axis 201, etc.) may be effected by causing the rotatable element 40, as well as the distal retention element 60 and/or the proximal retention element 70, to rotate (e.g., about longitudinal axis 41, etc.). In the illustrated embodiment, such rotation may be caused by moving the manual trigger 100 of the rooter 10's actuator 90 along the length of the rooter 10's housing 20. As the manual trigger 100 is moved along the length of the housing 20, the intermediate element 98 of the actuator 90 moves through the longitudinal slot 34 in the housing 20, which causes the cylindrical element 92 of the actuator 90 within the interior 24 of the housing to move along the length of the rotatable element 40. As the cylindrical element 92 moves along the length of the rotatable element 40, drive features 96 (FIGS. 8B and 8C) on or in the interior surface 95 of the aperture 94 of the cylindrical element 92 may engage the complementarily configured rotation facilitator 47 of the rotatable element 40 (e.g., the depicted helical ridge, etc.). The configurations of the longitudinal slot 34 and the actuator 90 (specifically, its intermediate element 98) may prevent rotation of the cylindrical element 92 of the actuator 90 within the interior 24 of the housing 20, or at least enable the rotatable element 40 to rotate relative to the housing 20. During rotation of the rotatable element 40, one or both of the distal retention element 60 and the proximal retention element 70 may rotate relative to the housing 20, which rotation may also cause the elongate medical instrument 200 to spin relative to the housing 20 of the rooter 10. If the rooter 10 is held stationary, or at least substantially stationary, movement of the manual trigger 100 of the actuator 90 of the rooter 10 may cause the elongate medical instrument 200 to rotate or spin relative to a subject's body. In other embodiments, the rooter 10 may be used to rotationally oscillate the elongate medical instrument 200, which may enhance the performance of the device. Rotation or oscillation of the elongate medical instrument 200 may be effected during or separately from longitudinal movement (e.g., distal movement, proximal movement, back-and-forth movement, etc.) of the elongate medical instrument 200.

When the proximal end 202 of a tubular elongate medical instrument 200 (e.g., a catheter, a tube, etc.) is accessible from or proximally beyond the proximal end of the rooter (e.g., beyond the proximal end 78 of the proximal retention element 70 of the rooter 10, etc.), other activities (e.g., aspiration, infusion, introduction of other elongate medical instrument 200, etc.) may be effected through the elongate medical instrument 200 while it is assembled with the rooter 10 and, in some embodiments, as the elongate medical instrument 200 is rotated, spun, or oscillated.

In various embodiments, a rooter 10 of the present invention may be used to enable or effect a variety of medical procedures. Without limiting the scope of the present invention, medical procedures in which a rooter may be useful include imaging, drug delivery, feeding, stimulation, recording, pacing, temperature sensing, tissue resection, and implant delivery.

In some embodiments, use of a rooter 10 to manipulate an elongate medical instrument 200 may facilitate introduction of the elongate medical instrument 200 into the body of a subject. In other embodiments, an elongate medical instrument 200 may be rotated, spun or oscillated with a rooter 10 to facilitate further introduction of the elongate medical instrument 200 into the body of a subject, or its removal from the subject's body.

In still other embodiments, rotation, spinning, or oscillation of an elongate medical instrument 200 may enable the removal of substances (e.g., clots, blockages, etc.) from the body of a subject or from another medical device (e.g., a tube, catheter, etc.) within the subject's body.

In some embodiments, when medical personnel introduce an elongate medical instrument 200 into the body of a subject through the skin, a natural orifice, a surgical access site, or other natural or man-made structure, they may encounter friction or obstructions. Some of the causes of friction or obstructions include, without limitation, tortuous pathways, lesions, viscous fluid (e.g., blood clots, etc.), other devices, and combinations of any of the foregoing. Use of a rooter 10 to twist, spin, or oscillate the elongate medical instrument 200 may counteract any friction that may be encountered as the elongate medical instrument 200 is introduced into the body, or during tracking to facilitate device introduction. As a non-limiting example, a rooter 10 may be used to torque a guide wire, which may enable the guide wire to drill through, or cross, lesions or occlusions within a subject's vasculature. In another example, a rooter 10 may rotate a catheter as the catheter is advanced over a wire into a subject's body, including situations where merely pushing the catheter will not cause it to advance along the wire.

Still another example of use of a rooter 10 includes rotation of a needle, such as a biopsy needle to facilitate the cutting and removal of tissue or another material from the body of a subject, to access (including intraosseous access, etc.) and/or sample bone marrow, a needle for use in spinal interventions, or a needle for providing general access to an internal location of a subject's body.

Use of a rooter 10 may also be useful for removing leads, such as those used with pacemakers or defibrillators. As leads are removed, rotation, spinning, or oscillation of the leads, or of a sheath that has been introduced over the leads, may cut endothelium or fibrin sheaths that may hinder removal of the leads from the subject's vasculature.

Although the foregoing description contains many specifics, these should not be construed as limiting the scope of the invention or of any of the appended claims, but merely as providing information pertinent to some specific embodiments that may fall within the scopes of the invention and the appended claims. Other embodiments of the invention may also be devised which lie within the scopes of the invention and the appended claims. Features from different embodiments may be employed in combination. The scope of the invention is, therefore, indicated and limited only by the appended claims and their legal equivalents. All additions, deletions and modifications to the invention, as disclosed herein, that fall within the meaning and scopes of the claims are to be embraced thereby.

What is claimed:

1. A rooter for manually spinning an elongate medical instrument with one hand, comprising:
   a cylindrical housing with a length and an elongated slot extending along the length;
   a rotatable element within an interior of the cylindrical housing, the rotatable element extending through an entirety of the length of the cylindrical housing, the rotatable element comprising a cylindrical element with a rotation facilitator comprising a helical ridge protruding from a surface of the cylindrical element, the helical ridge extending along a length of the interior of the cylindrical housing;
   a coupling feature on the rotatable element for rotatably engaging an elongate medical instrument;

an actuator configured to enable rotation of the rotatable element with one hand, including:
   a cylindrical element residing within the cylindrical housing, the cylindrical element:
surrounding the rotatable element;
configured to be translated along at least a portion of a length of the rotatable element through a length of the interior of the cylindrical housing;
including an aperture defining an interior surface of the cylindrical element, the interior surface defining a drive feature that complementarily engages the helical ridge of the rotation facilitator of the rotatable element and is configured to cause the rotatable element to rotate as the cylindrical element of the actuator is translated along at least a portion of the length of the rotatable element;
an intermediate portion of the actuator extending from the cylindrical element and through the elongated slot of the cylindrical housing; and
   an external element:
secured to the intermediate portion of the actuator outside of the cylindrical housing;
including a trigger protruding from the cylindrical housing;
configured to receive a digit of a hand of an individual;
configured to be translated along the length of the cylindrical housing by the digit; and
configured to translate the intermediate portion of the actuator along the elongated slot in the cylindrical housing and to translate the cylindrical element of the actuator along at least a portion of the length of the interior of the cylindrical housing;
   a coiled spring within the cylindrical housing and surrounding the rotatable element, a proximal end of the coiled spring abutting the cylindrical housing at a proximal end of an interior of the cylindrical housing, a distal end of the coiled spring abutting a proximal side of the cylindrical element of the actuator to apply a distally oriented biasing force against the cylindrical element of the actuator; and
   a handle fixedly secured to and protruding from a proximal location of the cylindrical housing on a same side of a circumference of the cylindrical housing as the external element of the actuator;
   a conduit extending through a length of the rotatable element and communicating with a distal end and a proximal end of the rooter for receiving the elongate medical instrument, wherein the rooter is configured to spin the elongate medical instrument during or separately from longitudinal movement of the elongate medical instrument.

2. The rooter of claim 1, further comprising:
a retention element at an end of the conduit configured to receive a portion of the elongate medical instrument and configured to engage an outer surface of the elongate medical instrument to hold at least the portion of the elongate medical instrument in place within the conduit.

3. A system for rotating an elongate medical instrument, comprising:
an elongate medical instrument including a distal end for insertion into the body of a subject and a proximal end; and
a rooter configured for manual operation and including:
a cylindrical housing with a length and an elongated slot extending along the length;
   a rotatable element within an interior of the cylindrical housing, the rotatable element extending through an entirety of the length of the cylindrical housing, the rotatable element comprising a cylindrical element with a rotation facilitator comprising a helical ridge protruding from a surface of the cylindrical element, the helical ridge extending along a length of the interior of the cylindrical housing;
   a coupling feature on the rotatable element for rotatably engaging an elongate medical instrument;
   an actuator configured to enable rotation of the rotatable element with one hand, including:
      a cylindrical element residing within the cylindrical housing, the cylindrical element:
surrounding the rotatable element;
configured to be translated along at least a portion of a length of the rotatable element through a length of the interior of the cylindrical housing;
including an aperture defining an interior surface of the cylindrical element, the interior surface defining a drive feature that complementarily engages the helical ridge of the rotation facilitator of the rotatable element and is configured to cause the rotatable element to rotate as the cylindrical element of the actuator is translated along at least a portion of the length of the rotatable element;
      an intermediate portion of the actuator extending from the cylindrical element and through the elongated slot of the cylindrical housing; and
      an external element:
secured to the intermediate portion of the actuator outside of the cylindrical housing;
including a trigger protruding from the cylindrical housing;
configured to receive a digit of a hand of an individual;
configured to be translated along the length of the cylindrical housing by the digit; and
configured to translate the intermediate portion of the actuator along the elongated slot in the cylindrical housing and to translate the cylindrical element of the actuator along at least a portion of the length of the interior of the cylindrical housing;
      a coiled spring within the cylindrical housing and surrounding the rotatable element, a proximal end of the coiled spring abutting the cylindrical housing at a proximal end of an interior of the cylindrical housing, a distal end of the coiled spring abutting a proximal side of the cylindrical element of the actuator to apply a distally oriented biasing force against the cylindrical element of the actuator; and
   a handle fixedly secured to and protruding from a proximal location of the cylindrical housing on a same side of a circumference of the cylindrical housing as the external element of the actuator;
   a conduit extending through a length of the rotatable element and communicating with a distal end and a proximal end of the rooter for receiving the elongate medical instrument, wherein the rooter is configured to rotate the elongate medical instrument during or separately from longitudinal movement of the elongate medical instrument.

4. The system of claim 3, wherein the elongate medical instrument comprises at least one of a needle, a drill bit, a trocar, a wire, a catheter, and a tube.

5. The system of claim 3, wherein the rotatable element is configured to enable a proximal end of the elongate medical instrument to extend proximally beyond the rooter.

6. The rooter of claim 3, further comprising:
a retention element at an end of the conduit configured to receive a portion of the elongate medical instrument and configured to engage an outer surface of the elongate medical instrument to hold at least the portion of the elongate medical instrument in place within the conduit.

7. The system of claim 6, wherein the elongate medical instrument comprises a catheter, a wire, a needle, a drill bit or a trocar.

* * * * *

UNITED STATES PATENT AND TRADEMARK OFFICE
CERTIFICATE OF CORRECTION

| | | |
|---|---|---|
| PATENT NO. | : 8,845,621 B2 | Page 1 of 1 |
| APPLICATION NO. | : 12/907926 | |
| DATED | : September 30, 2014 | |
| INVENTOR(S) | : Fojtik | |

It is certified that error appears in the above-identified patent and that said Letters Patent is hereby corrected as shown below:

In the Specification

Column 6, Line 7, change "20Q" to --200,--

Column 8, Line 8, change "50." to --40.--

Column 8, Line 15, change "rooter, 10'" to --rooter 10'--

Column 9, Line 6, insert --distal-- before "retention"

Signed and Sealed this
Third Day of February, 2015

Michelle K. Lee
*Deputy Director of the United States Patent and Trademark Office*